United States Patent [19]

Stütz et al.

[11] 4,147,789
[45] Apr. 3, 1979

[54] 6-METHYL-8-THIOMETHYL-ERGOLENE DERIVATIVES

[75] Inventors: Peter Stütz, Bottmingen; Paul Stadler, Biel-Benken, both of Switzerland

[73] Assignee: Sandoz Ltd., Basel, Switzerland

[21] Appl. No.: 726,981

[22] Filed: Sep. 27, 1976

Related U.S. Application Data

[63] Continuation-in-part of Ser. No. 556,336, Mar. 7, 1975, abandoned.

[30] Foreign Application Priority Data

Mar. 14, 1974 [CH] Switzerland ............... 3563/74
Jul. 23, 1974 [CH] Switzerland ............... 10138/74
Jan. 2, 1976 [GB] United Kingdom ............. 49/76

[51] Int. Cl.² .................... C07D 457/02; N61K 31/48
[52] U.S. Cl. ............................ 424/261; 424/249;
424/251; 544/219; 544/298; 544/316; 544/319;
546/67
[58] Field of Search ............ 260/285.5, 256.5 R,
260/249.8; 424/261, 249, 251; 544/219, 316,
319, 298

[56] References Cited

U.S. PATENT DOCUMENTS 3,901,894  8/1975  Kornfeld et al. ............... 260/285.5

FOREIGN PATENT DOCUMENTS 2509471  9/1975  Fed. Rep. of Germany ........ 260/285.5
3563     3/1974  Switzerland ................... 260/285.5

Primary Examiner—Donald G. Daus
Assistant Examiner—Mary C. Lee

Attorney, Agent, or Firm—Gerald D. Sharkin; Robert S. Honor; Thomas O. McGovern

[57] ABSTRACT

This invention provides new compounds of formula I,

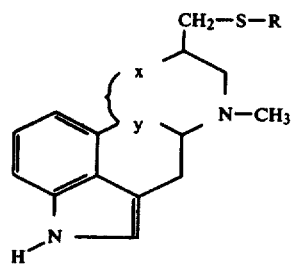

wherein
x̄ ȳ is the group

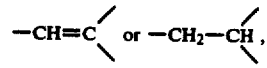

and
R is hydrogen, cyano, a 5- or 6-membered unsaturated heterocyclic radical attached through a ring carbon atom and having 1, 2 or 3 hetero ring atoms, the first hetero atom being nitrogen, oxygen or sulphur, and the second and third hetero atoms, if present, being nitrogen, or 2- or 4-pyridyl monosubstituted by lower alkyl, lower alkoxy or halogen, useful as anti-Parkinson agents.

36 Claims, No Drawings

6-METHYL-8-THIOMETHYL-ERGOLENE DERIVATIVES

This application is a continuation-in-part of our application Ser. No. 556,336 filed Mar. 7, 1975, now abandoned, the contents of which are incorporated herein by reference.

The present invention relates to new heterocyclic compounds.

In accordance with the invention there are provided new compounds of formula I,

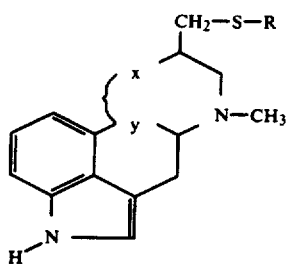

wherein
$\widehat{x\ y}$ is the group

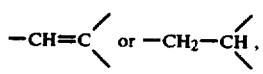

and

R is hydrogen, cyano, a 5- or 6-membered unsaturated heterocyclic radical attached through a ring carbon atom and having 1, 2 or 3 hetero ring atoms, the first hetero atom being nitrogen, oxygen or sulphur, and the second and third hetero atoms, if present, being nitrogen, or 2- or 4-pyridyl monosubstituted by lower alkyl, lower alkoxy or halogen.

When R is a heterocyclic radical, this is preferably fully unsaturated. R has preferably two double bonds when five-membered. R has preferably three double bonds when six-membered.

R has preferably one or two hetero atoms. When R has one hetero atom this is conveniently pyridyl or thienyl. When R has two hetero atoms, this is conveniently oxazolyl, thiazolyl, imidazolyl or pyrimidinyl. When R has three hetero atoms, this is conveniently 1,2,4-triazolyl, or 1,3,5-triazinyl.

The ring carbon atom through which R is attached is conveniently ortho or para to a ring hetero atom, e.g. 2-pyridyl or 4-pyridyl, 2-thiazoyl, or 1,2,4-triazol-3-yl.

When R is 2- or 4-pyridyl monosubstituted by lower alkyl, the alkyl substituent may, for example, contain 1 to 4, especially 1 or 2 carbon atoms and preferably signifies methyl.

When R is 2- or 4-pyridyl monosubstituted by lower alkoxy, the alkoxy substituent may, for example, contain from 1 to 4, especially 1 or 2 carbon atoms and preferably signifies methoxy.

When R is 2- or 4-pyridyl monosubstituted by halogen, the halogen may denote fluorine, bromine and especially chlorine.

The side chain in the 8 position of the ergolene moiety may be in the α- or β-configuration.

Any carbon containing radical not particularly defined herein preferably has up to 10 carbon atoms.

Further, in accordance with the invention a compound of formula I may be obtained by a process comprising (a) reacting a compound of formula II,

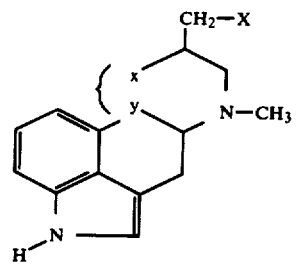

wherein
$\widehat{x\ y}$ is as defined above, and
X is an exchangeable radical capable of being displaced by a thio group
with a compound of formula III, $$MS-R \qquad III$$

wherein
R is as defined above, and
M is hydrogen or an alkali metal,
or (b) reducing the —SCN group to an —SH group in a compound of formula Ib,

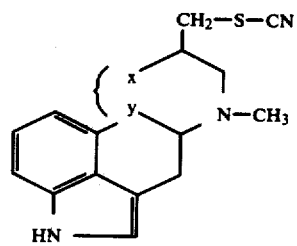

wherein
$\widehat{x\ y}$ is as defined above, to produce a compound of formula Ia,

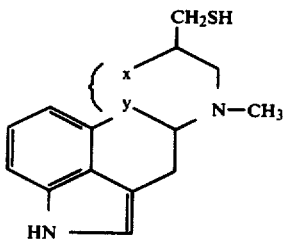

wherein
$\widehat{x\ y}$ is as defined above

Process variant (a) may be effected in conventional manner for nucleophilic substitution by a thio group, bearing in mind the other substituents present.

The radical X may, for example, signify halogen, such as chlorine or bromine, or a radical $O-SO_2-R_1$, wherein $R_1$ is lower alkyl or phenyl or substituted phenyl. It is preferred to use the corresponding mesylate or tosylate as compound of formula II.

In general M in the compounds of formula III preferably denotes an alkali metal, especially when R is not basic, i.e., has no basic nitrogen atom.

The reaction is conveniently effected in a solvent. Specially suitable are inert, aprotic, polar solvents, e.g. amides of organic carboxylic acids, such as dimethyl formamide, or alternatively hexamethylphosphoric acid triamide or acetonitrile, optionally admixed with a small portion of water.

The reaction is preferably effected at an elevated temperature, e.g. between about 50° and 100° C.

The reaction is conveniently effected in the absence of oxygen, e.g. in an atmosphere of nitrogen.

It is convenient to use an excess of the compound of formula III, e.g. about 2 to 10 mols of the compound of formula III, for each mol of the compound of formula II.

The reduction of compounds of formula Ib to compounds of formula Ia may be effected in a manner analogous to known methods for the reduction of similar cyanate compounds to mercapto compounds, bearing in mind the other substituents present. However, it is preferably effected with lithium aluminium hydride. In this case an ether, such as tetrahydrofuran, is especially used as solvent.

The reduction with lithium aluminium hydride may be effected at room temperature.

The working up of the reaction mixture obtained in accordance with the above processes and the purification of the so obtained compounds of formula I may be effected in accordance with known methods.

The compounds of formula I may be present in free form or in the form of acid addition salts thereof. Acid addition salt forms may be produced from the free bases in known manner and vice versa. A suitable acid for salt formation is tartaric or fumaric acid.

The starting materials of formula II wherein X is chlorine, O-mesyl or O-tosyl, are known.

Compounds of formula II wherein X is bromine, may, for example, be obtained by reaction of a compound of formula IV,

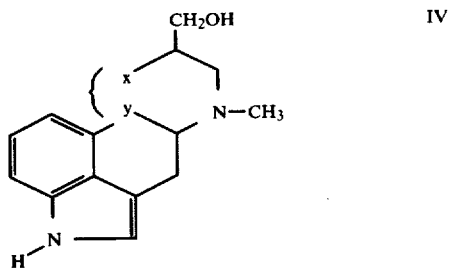

wherein x⁀y is as defined above, with phosphorus oxybromide.

Insofar as the production of the starting materials is not described, these are known or may be produced in accordance with known processes, or in a manner analogous to the processes described herein or to known processes.

The compounds of formula I are furthermore useful as anti-Parkinson agents, as indicated by central dopaminergic stimulating activity which is for example ascertained in rats in which a unilateral degeneration of the nigro-neostriatal dopamine track has been brought about by a 6-hydroxy-dopamine injection in the Substantia nigra [method of U. Ungerstedt, Acta physiol. scand., Suppl. 367, 69-93 (1971)]. The so "denervated" dopamine receptors when stimulated with dopaminergic compounds, show an increased sensitiveness which is recognizable by the fact that the rats perform turning movements in the direction of the non-"denervated" side. These movements are observed after administration of the compounds of formula I at a dose of approximately 0.3 to about 3 mg/kg s.c., and approximately 5 mg/kg to about 10 mg/kg p.o., animal body weight of the compounds.

Additionally the central dopaminergic stimulating activity is indicated by the inhibition of reserpine induced catalepsy in mice on s.c. administration of from about 0.3 to about 3 mg/kg animal body weight of of the compounds, the reserpine being administered i.p. at 5 mg/kg animal body weight about 17 hours before the test substance and the catalepsy being considered antagonised if the mice can walk off a horizontal twine covered pole in a coordinated manner.

For this use the dosage will, of course, vary depending on the compound employed, mode of administration and treatment desired. However, in general, satisfactory results are obtained when administered at a daily dosage of from about 0.02 mg to about 10 mg per kg animal body weight, conveniently given in divided doses 2 to 5 times a day or in sustained release form. For the larger mammals, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

The compounds of formula I may be administered in pharmaceutically acceptable acid addition salt form. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutical carrier or diluent.

Such compositions may be made in conventional manner to be in the form of, for example, a solution or a tablet. Representative acid addition salt forms include organic acid salt forms such as the hydrogen maleate, fumarate, tartrate and methan sulphonate and mineral acid salt forms such as the hydrochloride, hydrobromide and sulphate.

Combinations of a compound of formula I and a phosphodiesterase inhibitor are especially useful in the treatment of Morbus Parkinson because the central dopaminergic stimulant activity of a compound of formula I is synergistically potentiated when administered concomitantly with an inhibitor of phosphodiesterase activity, as indicated by a super-additive increase in turning movements in the above-indicated test when a compound of formula I is administered after i.p. administration of from about 5 to about 25 mg/kg animal body weight of an inhibitor of phosphodiesterase activity, the compound of formula I being administered p.o. at from about 1 to about 5 mg/kg animal body weight.

For this use the dosage will, of course, vary depending on the compound employed, mod of administration and treatment desired. However, in general, satisfactory results are obtained when administered at a daily dosage of from about 0.01 mg to about 1 mg per kg animal body weight, conveniently given in divided doses 2 to 5 times a day or in sustained release form. For the larger mammals, the total daily dosage is in the range from about 0.5 to about 50 mg, and dosage forms suitable for oral administration comprise from about 0.1 mg to about 25 mg of the compounds admixed with a solid or liquid pharmaceutical carrier or diluent.

A satisfactory ratio of formula I compound to phosphodiesterase inhibitor is from about 10:1 to about 1:5000, preferably 2:1 to 1:1000, e.g. 1:50 to 1:1, e.g. 1:5 to 1:1, 1:25 or 1:10 to 1:50.

Suitable phosphodiesterase inhibitors are especially those which inhibit phosphodiesterase activity in the brain, e.g. methyl xanthines such as caffeine or theophylline, but also may be chosen from derivatives of 4-amino-1H-pyrazolo[3,4-b]pyridine-5-carboxyclic acid esters, such as 1-ethyl-4-(isopropylidene-hydrazino)-1H-pyrazolo[3,4-b]pyridine-5-carboxylic acid ethyl ester, 1-ethyl-4-hydrazino-1H-pyrazolo[3,4-b]pyridine-5-carboxylic acid ethyl ester and 1-ethyl-4-butylamino-1-ethyl-1H-pyrazolo[3,4-b]pyridine-5-carboxylic acid ethyl ester, 4-(3,4-dimethoxybenzyl)-2-imidazolidinone and analogues thereof, such as 4-(3-butoxy-4-methoxybenzyl)-2-imidazolidinone, minor tranquilizers, e.g. of the 1,4-benzodiazepine series, such as 7-chloro-2-methylamino-5-phenyl-3H-1,4-benzodiazepine-4-oxide and 7-chloro-1,3-dihydro-1-methyl-5-phenyl-2H-1,4-benzodiazepin-2-one, tricyclic antidepressants, such as 4-[3-(5H-dibenz[b,f]azepin-5-yl)propyl]-1-piperazine ethanol, phenothiazines such as 4-{3-[2-(trifluoromethyl)phenothiazin-10-yl]propyl}-1-piperazine ethanol and 2-chloro-10-(3-dimethylaminopropyl)phenothiazine, 2,6-bis-(diethanolamino)-4,8-dipiperidinopyrimidino[5,4-b]pyrimidine and papaverine.

The present invention also provides a pharmaceutical package containing as active agents a compound of formula I and an inhibitor of phosphodiesterase activity, the active agents being admixed or kept separate until required for concomitant administration.

It is contemplated that all the usual pharmaceutical compositions may be made to encompass the above-indicated two active agents, e.g. tablets, powders, granulates, capsules, sirups and elixirs for oral administration, as well as solutions, dispersions and emulsions for parenteral administration. It is also contemplated that these compositions may be made in conventional manner using conventional pharmaceutical carriers and diluents.

Accordingly the present invention also provides a process for the production of a pharmaceutical composition including the step of bringing a compound of formula I as one active agent into association with an inhibitor of phosphodiesterase activity as another active agent, the active agents being sufficiently pure for pharmaceutical acceptability.

It will be appreciated that combinations of a compound of formula I and a phosphodiesterase inhibitor may be conveniently administered in unit dosage form 2 to 5 times a day or in sustained release form. Such combinations may contain for example from about 0.1 to about 25 mg of a compound of formula I and the appropriate amount of phosphodiesterase inhibitor to give the indicated ratio range mentioned above.

The compounds of formula I wherein $\widehat{x\quad y}$ is

exhibit especially interesting central dopaminergic stimulating properties. R preferably signifies the 2-pyridyl or cyano group.

In one group of compounds R is hydrogen cyano or a heterocyclic as defined above. In another group of compounds R is cyano, 4-pyridyl or 2-thiazoyl.

In the following non-limitative Examples all temperatures are indicated in degrees Centigrade.

EXAMPLE 1

6-methyl-8β-thiocyanomethylergolene[process variant (a)]

4.5 g (13.5 millimols) of 6-methyl-8β-methanesulphonyloxymethylergolene are heated together with 4.5 g (approx. 46 millimols) of potassium thiocyanate in a mixture of 45 cc of hexamethylphosphoric acid triamide and 3 cc of water to 80° under a stream of nitrogen for 20 hours. Working up is effected by pouring the reaction mixture into 450 cc of a 0.5 normal soda solution and filtering. The dry residue is dissolved whilst hot in a mixture of methylene chloride/ether and treated with active charcoal. The filtrate is concentrated and the title compound is obtained by crystallization from ethanol in the form of pink-tinged prisms having a M.P. of 186°–188°.

Hydrogen fumarate: from methylene chloride/ethanol, M.P. 182°–184°; $[\alpha]_D^{20} = +55°$ (c = 0.5, dimethyl formamide).

EXAMPLE 2

6-methyl-8β-mercaptomethylergolene 4.5 g (approx. 60 millimols) of sodium hydrogen sulphide · H₂O are used in a manner analogous to that described in Example 1. After working up rapidly, the crystalline title compound is obtained from methylene chloride/isopropanol; decomposition point approx. 200°, $[\alpha]_D^{20} = +86°$ (c = 0.5, dimethyl formamide).

The following compounds of formula I are obtained in a manner analogous to that described in Example 1, using the corresponding starting materials of formulae II and III:

EXAMPLE 3

6-methyl-8β-(2-pyridyl-thiomethyl)ergolene

M.P. 200°–201° (decomp.)

Tartrate: M.P. 195°–196°; $[\alpha]_D^{20} = +26°$ (c = 1, dimethyl sulphoxide) (using 2-mercaptopyridine as compound of formula III).

EXAMPLE 4

6-methyl-8β-(2-pyridyl-thiomethyl)ergoline-I

M.P. 191°–195°; $[\alpha]_D^{20} = -113°$ (c = 1, pyridine).

EXAMPLE 5

6-methyl-8β-(4-pyridyl-thiomethyl)ergolene

M.P. 191°–194°; $[\alpha]_D^{20} = +52.5°$ (c = 1, dimethyl sulphoxide).

EXAMPLE 6

6-methyl-8β-(2-thiazolyl-thiomethyl)ergolene

M.P. 192°–195° (decomp.); $[\alpha]_D^{20} = +58.2°$ (c = 1, dimethyl sulphoxide).

EXAMPLE 7

6-methyl-8β-thiocyanomethylergoline-I

M.P. 189°–193°; $[\alpha]_D^{20}$ = −58° (c = 1, dimethyl sulphoxide).

EXAMPLE 8

6-methyl-8α-thiocyanomethylergoline-I

M.P. 185°–188°.

EXAMPLE 9

6-methyl-8β-(2-thienyl-thiomethyl)ergolene

EXAMPLE 10

6-methyl-8β-(2-oxazolyl-thiomethyl)ergolene

EXAMPLE 11

6-methyl-8β-(2-imidazolyl-thiomethyl)ergolene

EXAMPLE 12

6-methyl-8β-(2-pyrimidinyl-thiomethyl)ergolene

EXAMPLE 13

6-methyl-8β-[3-(1,2,4-triazolyl)thiomethyl]ergolene

EXAMPLE 14

6-methyl-8β-[2-(1,3,5-triazinyl)thiomethyl]ergolene

EXAMPLE 15

6-methyl-8β-[2-(4-methylpyridyl)thiomethyl]ergolene

EXAMPLE 16

6-methyl-8β-[2-(4-methoxypyridyl)thiomethyl]ergolene

EXAMPLE 17

6-methyl-8β-[4-(2-chloropyridyl)thiomethyl]ergolene

EXAMPLE 18

6-methyl-8β-(3-pyridylthiomethyl)ergolene $[\alpha]_D^{20}$ = +38° (c = 0.5 in DMF), M.Pt. 192°–196° C.[1]

[1] in the form of the free base.

EXAMPLE 19

6-methyl-8α-(2-pyridylthiomethyl)ergoline-I $[\alpha]_D^{20}$ = −58° (c = 0.6 in DMF), M.Pt. 195°–197° C.[1]

[1] in the form of the free base.

EXAMPLE 20

6-methyl-8α-(2-pyridylthiomethyl)ergolene $[\alpha]_D^{20}$ = +185° (c = 0.3 in DMF), M.Pt. 220°–224° C.[2]

[2] in the form of the dihydrochloride.

EXAMPLE 21

6-methyl-8β-mercaptomethylergolene [process (b)]

11.8 g (40 millimols) of 6-methyl-8β-thiocyanomethyl-9-ergolene are added portionwise at room temperature to a suspension stirred under nitrogen of 15.1 g (0.4 millimols) of lithium aluminium hydride in 800 cc of absolute tetrahydrofuran, and stirring is effected for one hour at this temperature. Working up is effected by carefully decomposing with water while cooling well and stirring into 500 cc of a 5% aqueous tartaric acid solution. The reaction mixture is subsequently rendered alkaline with a potash solution and the aqueous phase is rapidly extracted with methylene chloride containing 10% of methanol. After drying over sodium sulphate and removing the solvent by distillation, the title compound is obtained.

Decomp. approx. 200°, $[\alpha]_D^{20}$ = +86° (c = 0.5, dimethyl formamide).

EXAMPLE 22

6-methyl-8α-methanesulphonyloxymethylergoline-I (starting material for Example 8)

A solution of 1.95 cc (25 millimols) of methanesulphonyl chloride in 5 cc of absolute acetonitrile is added dropwise at +10° to a stirred suspension of 2.56 g (10 millimols) of 9,10-dihydro-isolysergol I [Helv. 32, 1947 (1949)] in 15 cc of absolute pyridine and 25 cc of absolute acetonitrile, and stirring is effected at room temperature for one hour. Working up is effected by cooling to 0°, diluting with methanol until a clear solution is obtained, rendering alkaline and distributing between 2N ammonia/methylene chloride. After drying and concentrating the combined organic phases by evaporation, 6-methyl-8α-methanesulphonyloxymethyl-ergoline-I crystallizes from ethanol.

M.P. 139°–141°, $[\alpha]_D^{20}$ = −54.6° (c = 1, dimethyl formamide).

EXAMPLE 23

Production of a solid pharmaceutical preparation (a) 1 mg of a compound of formula I is mixed with lactose and optionally with 25 mg of a phosphodiesterase inhibitor. The mixture is granulated with water, 0.5% sodium alginate or 1% gelatin solution. The dry granulate is pressed into tablets in the presence of some tartaric acid, approx. 5% of talc, about 5% of maize starch and approx. 0.1% of magnesium stearate.

In this manner it is possible to obtain, for example, tablets having the following composition:

| Compound of formula I | 1 | mg | 1 | mg |
|---|---|---|---|---|
| Phosphodiesterase inhibitor | — | mg | 25 | mg |
| Lactose | 85.9 | mg | 60.9 | mg |
| Tartaric acid | 3 | mg | 3 | mg |
| Maize starch | 5 | mg | 5 | mg |
| Talc | 5 | mg | 5 | mg |
| Magnesium stearate | 0.1 | mg | 0.1 | mg |
| Tablet of | 100.0 | mg | 100.0 | mg |

(b) Capsules

The capsules may contain the active agent or agents alone. The following capsules may, for example, be obtained in accordance with known methods:

| Compound of formula I | 5 | mg | 5 | mg |
|---|---|---|---|---|
| Phosphodiesterase inhibitor | 50 | mg | — | mg |
| Diluent (e.g. kaolin) | — |  | 295 | mg |
| Capsule content of | 55 | mg | 300 | mg |

EXAMPLE 24

Production of a liquid pharmaceutical preparation

A liquid preparation, e.g. a suspension suitable for oral administration, may contain a compound of formula I and a phosphodiesterase inhibitor together with an inert, pharmaceutically tolerable liquid solvent or carrier material. It may further contain other additives, e.g. sweetening and colouring agents, flavourings and stabilizing agents.

The following oral suspension may, for example, be obtained using known methods:

| Compound of formula I | 1.0 | mg | 1 | mg |
|---|---|---|---|---|
| Phosphodiesterase inhibitor | — | | 10 | |
| Vanilla essence | q.s. | | q.s. | |
| Colouring agent | q.s. | | q.s. | |
| Buffer | q.s. | | q.s. | |
| Water | q.s. | up to 5 cc | q.s. | up to 5 cc |

The preferred compounds of formula I for use in Examples 23 and 24 are 6-methyl-8β-thiocyanomethylergolene and 6-methyl-8β-(2-pyridyl-thiomethyl)ergolene.

The preferred phosphodiesterase inhibitors for use in Examples 23 and 24 are theophylline and caffeine.

We claim:

1. A compound of formula I,

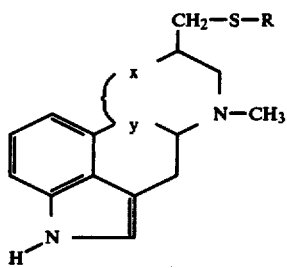

wherein
x⌢y is the group

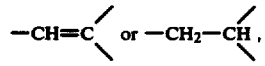

and

R is pyridyl, thienyl, oxazolyl, thiazolyl, imidazolyl, pyrimidinyl, 1,2,4-triazolyl or 1,3,5-triazinyl or 2- or 4-pyridyl mono-substituted by lower alkyl of 1 to 4 carbon atoms, lower alkoxy of 1 to 4 carbon atoms or fluorine, chlorine, or bromine, or a pharmaceutically acceptable acid addition salt thereof.

2. A compound of claim 1, wherein x⌢y is

3. A compound of claim 1, wherein R is pyridyl or thienyl.

4. A compound of claim 1, wherein R is pyridyl.

5. A compound of claim 1, wherein R is 2- or 4-pyridyl.

6. A compound of claim 5, wherein x⌢y is

7. A compound of claim 5, wherein x⌢y is

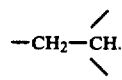

8. A compound of claim 1, wherein R is 4-pyridyl or 2-thiazoyl.

9. A compound of claim 1, wherein R is 1,2,4-triazol-3-yl.

10. A compound of claim 1, wherein R is oxyzolyl, thiazolyl, imidazolyl or pyrimidinyl.

11. A compound of claim 1, wherein R is 1,2,4-triazolyl or 1,3,5-triazinyl.

12. A compound of claim 1, wherein R is 2- or 4-pyridyl mono-substituted by alkyl of 1 to 4 carbon atoms.

13. A compound of claim 1, wherein R is 2- or 4-pyridyl mono-substituted by alkoxy of 1 to 4 carbon atoms.

14. A compound of claim 1, wherein R is 2- or 4-pyridyl mono-substituted by fluorine, chlorine or bromine.

15. The compound of claim 1, which is 6-methyl-8β-(2-pyridyl-thiomethyl)-ergoline-I.

16. The compound of claim 1, which is 6-methyl-8β-(2-pyridyl-thiomethyl)-ergolene.

17. The compound of claim 1, which is 6-methyl-8β-(4-pyridyl-thiomethyl)-ergolene.

18. The compound of claim 1, which is 6-methyl-8β-(2-thiazolyl-thiomethyl)-ergolene.

19. The compound of claim 1, which is 6-methyl-8β-(2-thienyl-thiomethyl)ergolene.

20. The compound of claim 1, which is 6-methyl-8β-(2-oxazolyl-thiomethyl)ergolene.

21. The compound of claim 1, which is 6-methyl-8β-(2-imidazolyl-thiomethyl)-ergolene.

22. The compound of claim 1, which is 6-methyl-8α-(2-pyrimidinyl-thiomethyl)-ergolene.

23. The compound of claim 1, which is 6-methyl-8β-[3-(1,2,4-triazolyl)thiomethyl]-ergolene.

24. The compound of claim 1, which is 6-methyl-8β-[-(1,3,5-triazinyl)thiomethyl]-ergolene.

25. The compound of claim 1, which is 6-methyl-8β-[2-(4-methylpyridyl)thiomethyl]-ergolene.

26. The compound of claim 1, which is 6-methyl-8β-[2-(4-methoxypyridyl)thiomethyl]-ergolene.

27. The compound of claim 1, which is 5-methyl-8β-[4-(2-chloropyridyl)thiomethyl]ergolene.

28. A pharmaceutical composition useful in treating Morbus Parkinson comprising 1 to 100 milligrams of a compound of claim 1, having the formula

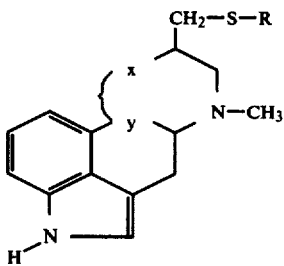

wherein
x⌢y is the group

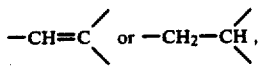

and

R is pyridyl, thienyl oxazolyl, thiazolyl, imidazolyl, pyrimidinyl, 1,2,4-triazolyl or 1,3,5-triazinyl or 2- or 4-pyridyl mono-substituted by alkyl of 1 to 4 carbon atoms, alkoxy of 1 to 4 carbon atoms, fluorine, chlorine or bromine, or a pharmaceutically acceptable acid addition salt thereof, in association with a pharmaceutical carrier.

29. A pharmaceutical composition according to claim 28, incorporating additionally a phosphodiesterase inhibitor selected from the group consisting of 1-ethyl-4-(isopropylidene-hydrazino)-1H-pyrazolo[3,4-b]-pyridine-5-carboxylic acid ethyl ester; 1-ethyl-4-hydrazino-1H-pyrazolo[3,4-b]pyridine-5-carboxylic acid ethyl ester; 1-ethyl-4-butylamino-1-ethyl-1H-pyrazolo[3,4-b]pyridine-5-carboxylic acid ethyl ester; 4-(3,4-dimethoxybenzyl)-2-imidazolidinone; 4-(3-butoxy-4-methoxy-benzyl)-2-imidazolidinone; 7-chloro-2-methylamino-5-phenyl-3H-1,4-benzo-diazepine-4-oxide; 7-chloro-1,3-dihydro-1-methyl-5-phenyl-2H-1,4-benzodiazepin-2-one; 4-[3-(5H-dibenz[b,f]-azepin-5-yl)propyl]-1-piperazine ethanol; 4-[3-(2-trifluoromethyl)phenothiazin-10-yl]-propyl]-1-piperazine ethanol; 2-chloro-10-(3-dimethylaminopropyl)phenothiazine-2,6-bis-(diethanolamino)-4,8-dipiperidino-pyrimidino-[5,4-d]pyrimidine and papaverine, in a ratio by weight of the compound of claim 28 to phosphodiesterase inhibitor of 10 to 1 to 1 to 5,000.

30. A pharmaceutical composition according to claim 28 comprising 0.2 to 50 milligrams of the compound per unit dosage.

31. A pharmaceutical composition according to claim 30 in which the compound is 6-methyl-8β-(2-pyridylthiomethyl)-ergolene.

32. A method of treating Morbus Parkinson in animals which comprises administering to an animal in need of such treatment a therapeutically effective amount of a compound of the formula

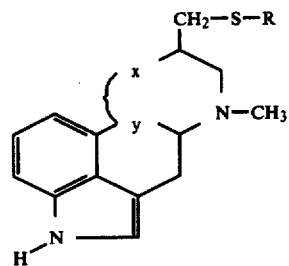

wherein
$\overbrace{x \quad y}$ is the group

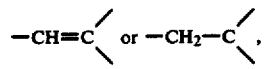

and

R is hydrogen, cyano, pyridyl, thienyl, oxazolyl, thiazolyl, imidazolyl, pyrimidinyl, 1,2,4-triazolyl or 1,3,5-triazinyl or 2- or 4-pyridyl mono-substituted by alkyl of 1 to 4 carbon atoms, alkoxy of 1 to 4 carbon atoms, fluorine, chlorine or bromine, or a pharmaceutically acceptable acid addition salt thereof.

33. A method according to claim 32, in which 1 to 100 milligrams of the compound are administered daily.

34. A method according to claim 32, in which 0.2 to 50 milligrams of the compound are administered per unit dosage.

35. A method according to claim 32, in which R is pyridyl or 2- or 4-pyridyl mono-substituted by lower alkyl, lower alkoxy or halogen.

36. A method according to claim 32, in which the compound is 6-methyl-8β-(2-pyridyl-thiomethyl)-ergolene.

* * * * *